United States Patent [19]

Muraoka

[11] Patent Number: 5,619,319
[45] Date of Patent: Apr. 8, 1997

[54] APPARATUS FOR ACQUIRING DATA USED TO EVALUATE AND REPRODUCE THE COLOR OF A SAMPLE ON THE BASIS OF THE CHROMA AND GLOSSINESS OF THE SAMPLE

[75] Inventor: Tetsuya Muraoka, Hamamatsu, Japan

[73] Assignee: Sanmei Electronic Co., Ltd., Shimizu, Japan

[21] Appl. No.: 207,088

[22] Filed: Mar. 8, 1994

[30]  Foreign Application Priority Data

Aug. 11, 1993 [JP] Japan .................................. 5-217962

[51] Int. Cl.$^6$ ........................ G01N 21/27; G01N 21/57
[52] U.S. Cl. ............................................. 356/73; 356/406
[58] Field of Search ...................................... 356/73, 406

[56]  References Cited

U.S. PATENT DOCUMENTS 4,853,879  8/1989  Matzoll, Jr. et al. .................. 356/73 X
4,886,355  12/1989  Keane ....................................... 356/73

FOREIGN PATENT DOCUMENTS 4-232821  8/1992  Japan .

OTHER PUBLICATIONS

IEEE, (1992 International Conference on Industrial Electronics, Control, Instrumentation, and Automation, pp. 706–708, "Trial Production of the Automatic Color Difference Discrimination System Based on the Dark Eyes' Color Perception", Muraoka, et al.

IEEE, (1993 Industry Applications Society) pp. 1761–1768, "Development and Practical Use of the Automatic Color and Glossiness Differences' Discrimination System Adapted to the Dark Eyes' Color and Light Sensations", Muraoka, et al.

Primary Examiner—Vincent P. McGraw
Attorney, Agent, or Firm—Spencer & Frank

[57]  ABSTRACT

Apparatus for acquiring both color and glossiness of a sample such as a painted material in order to inspect the quality of their color and glossiness by comparing them with those of another sample. The apparatus mainly consists of a standard light source, chroma sensing means, glossiness sensing means, decision data storing means storing various color and glossiness data together with a computer program, and a CPU for the comparison of data. The apparatus can be used for color reproduction in the automobile industry.

4 Claims, 5 Drawing Sheets

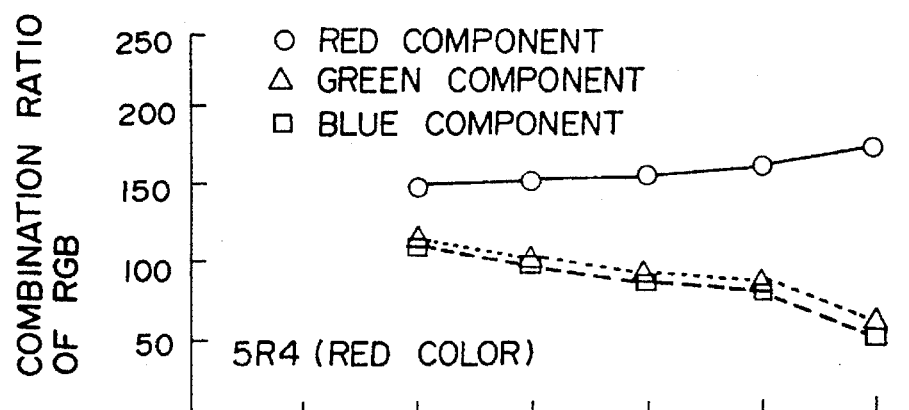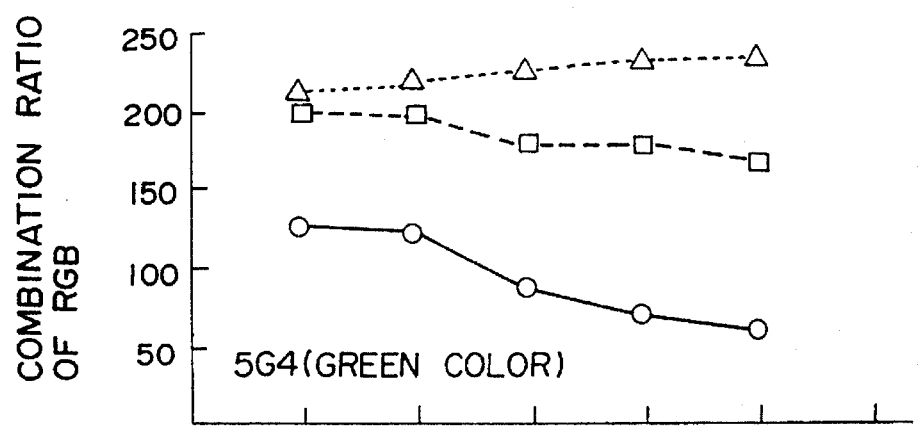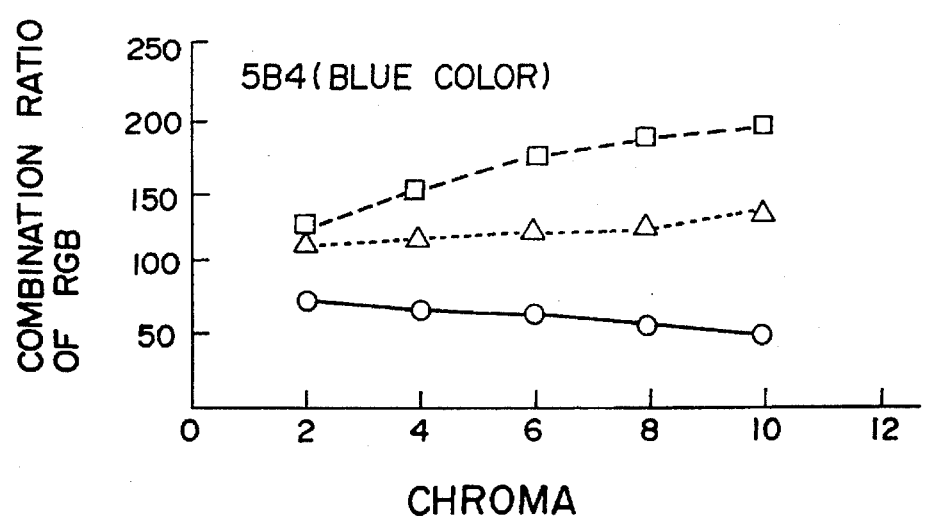

APPARATUS FOR ACQUIRING DATA USED TO EVALUATE AND REPRODUCE THE COLOR OF A SAMPLE ON THE BASIS OF THE CHROMA AND GLOSSINESS OF THE SAMPLE

BACKGROUND OF THE INVENTION

This invention relates to apparatus for acquiring data used to evaluate and reproduce the color of a sample on the basis of the chroma and glossiness of the sample.

The inventor of the present invention has carried out studies on the automatic decision of colors, on the detection of unevenness in colors of painted materials, and on the permissible range of unevenness.

Based on these studies, the inventor found that the grade of unevenness in colors which can be perceived by the eyes of a normal human being depends on the race to which the human being belongs (or on the color of the eyes). The normal human being described here implies an adult with no ophthalmic disease, who belongs to a group of adults with the same eye color, excepting those who have received special training. In relation to this knowledge, the inventor of the present invention published a paper "Automatic color Difference Discrimination System with Capability of the Dark Eyes' Color Perception," appearing in the Record of the 1EEE Conference on TENCON '91, New Delhi, India, vol. 3, pp. 401–404, August 1991. In addition, the automatic color difference discrimination system which was developed in accordance with the principle of operation of that paper was disclosed as Japanese patent disclosure number 232821 in 1992.

The color difference threshold, as appearing in the patent disclosure with Japanese patent disclosure number 232821 in 1992, was measured in accordance with the color difference by the method of constant stimuli in order to find the range of the color difference threshold. The standard stimuli for obtaining the range of the color difference threshold was generated by passing a light beam through interference filters with center frequencies of 430 nm (purple), 480 nm (blue), 535 nm (green), 580 nm (yellow), 600 nm (orange), and 655 nm (red).

FIG. 1 shows the average of the measured values of the color difference threshold at specific light wavelength, and the 95% confidence interval of these value.

The lower and upper boundaries to the subjective equivalent color in terms of the wavelength were thus obtained from the plots of FIG. 1 when the standard stimuli was given.

The interval between the lower and upper boundaries to the subjective equivalent color in terms of the specific wavelength gradually decreases with the wavelength increasing from purple to yellow, and reaches the minimum at the wavelength of orange. This interval then increases with the increasing wavelength starting from orange until arriving at the wavelength of red.

The interpolating method applies to the lower and upper boundaries to the subjective equivalent color, which are given in terms of the wavelength, so that a set of regression curves with minimum standard deviations could be obtained. Expressions (1) and (2) represent the regression curves for the upper ($Y_1$) and lower ($Y_2$) boundaries, respectively.

For the upper boundary ($Y_1$) to the subjective equivalent color, expression (1) is given as $$Y_1 = 2.18 \times 10^{-6} X^3 - 2.36 \times 10^{-3} X^2 + 1.63 X \quad (1)$$

For the lower boundary ($Y_2$) to the subjective equivalent color, expression (2) is $$Y_2 = 1.95 \times 10^{-4} X^2 + 0.88 X \quad (2)$$

Both $Y_1$ and $Y_2$ are valid for the wavelengths in the range of 410 nm to 670 nm.

The interval in wavelength, which is defined by a set of expressions (1) and (2), indicates the threshold to discriminate the subjective equivalent color in terms of the specific wavelength.

SUMMARY OF THE INVENTION

The inventor of the present invention proposed the improved device and method of acquiring data used to evaluate or reproduce the colors of a sample on the basis of the chroma and glossiness of the sample, so that said improved device and method can be used to improve the processes of painting colors in the automobile industry or those after a defective portion of an automobile is fixed.

Experiments were carried out to acquire basic data in terms of the chroma and glossiness (i.e., hue, lightness, saturation, and wavelength) by the use of a newly developed glossiness meter in addition to the use of the automatic color difference discrimination system which was proposed in the prescribed invention.

Data relating to glossiness needs to be acquired for the evaluation and reproduction of the color of a sample. The mixing of color materials is confirmed to be necessary for reproducing chroma and glossiness; however, it is not currently possible in practice to carry out this type of work in the field. This type of work has been carried out based on the experience and intuition of skillful painting craftsmen, as described heretofore.

The primary objective of the present invention is to provide apparatus for acquiring data used to evaluate and reproduce the color of a sample where said color seems to be the same as that of another sample when referring to the chroma and glossiness of the latter sample.

The apparatus for acquiring data for the evaluation and reproduction of the color of a sample on the basis of the chroma and glossiness of the sample, which is fabricated to accomplish the objective of the present invention, is composed of a standard light source to illuminate the sample; chroma sensing means to acquire data (Xso and Yso) by means of a plurality of chroma sensors (Xs and Ys) installed therein, each having different spectral sensitivity, when the sample is exposed to the light from said standard light source; glossiness sensing means to acquire data (Glo.) for said sample upon receiving the reflected component of light from said sample; decision data storing means to store decision data (Glo. vs Xso, and Yso) which has been acquired from both said chroma sensing means and said glossiness sensing means for each of a plurality of mark plates prepared for a variety of different colors and for a variety of different glossiness (Glo.); and arithmetic operation means to acquire by performing the arithmetic operation the outputs (XsoP and YsoP) of said color sensors at the time that an arbitrary sample is set at a specified glossiness (Glo. P), referring to data (Glo, vs Xso and Yso) obtained from both said chroma sensing means and said glossiness sensing means when said arbitrary sample is exposed to the light from said standard light source and also referring to decision data obtained from said decision data storing means.

The standard light source for illuminating said sample can be a Xenon lamp.

Said chroma sensing means can be a CCD color imager which outputs the colors of the sample.

Said glossiness sensing means can comprise said CCD color imager used as a reflected light sensor.

The apparatus for acquiring data for the reproduction of data of a sample or for the evaluation of data of three prime colors of the sample on the basis of chroma and glossiness of the sample in accordance with the present invention is composed of a standard light source to illuminate the sample; chroma sensing means to acquire data (Rso, Gso, and Bso) by means of a plurality of three prime color sensors (Rs, Gs, and Bs), each having different spectral sensitivity for one of the three prime colors, when the sample is exposed to said standard light source; glossiness sensing means to acquire data (Glo.) for said sample upon receiving the reflected component of light from said sample exposed to the light from said standard light source; decision data storing means to store decision data (Glo. vs Rso, Gso, and Bso) which has been acquired from both said chroma sensing means and said glossiness sensing means for each of a plurality of mark plates prepared for a variety of different colors and for a variety of different glossiness (Glo.); and arithmetic operation means to acquire by performing the arithmetic operation the outputs (RsoP, GsoP, and BsoP) of said color sensors at the time that said arbitrary sample is set at specified glossiness (Glo. P), referring to data (Glo. vs Rso, Gso, and Bso) obtained from both said chroma sensing means and said glossiness sensing means when said arbitrary sample is exposed to the light from said standard light source, and also referring to decision data obtained from said decision data storing means.

The apparatus of acquiring data for the evaluation of a sample by means of the specific eyes and for the reproduction of the sample on the basis of the chroma and glossiness of the sample in accordance with the present invention is composed of a standard light source to illuminate the sample; color sensing means to acquire data (Xso and Yso) by means of a plurality of chroma sensors (Xs and Ys) installed therein, each having different spectral sensitivity, when the sample is exposed to the light from said standard light source; glossiness sensing and output means consisting of glossiness sensing means to acquire data (Glo.) for said sample upon receiving the reflected component of light from said sample; decision data storing means to store decision data ($\lambda sXso$ and $\lambda sYso$) which has been acquired from a plurality of color sensors (Xs and Ys) for each of a plurality of wavelengths within the specified measuring range, decision data consisting of a plurality of color difference thresholds for each of a plurality of wavelengths, and to store decision data (Glo. vs Xso and Yso) which has been acquired from said glossiness sensing and output means for each of a plurality of mark plates prepared for a variety of different colors and for a variety of different glossiness (Glo.); and arithmetic operation means to acquire by performing the arithmetic operation the outputs (Xso0 and Yso0) of said color sensors at the time that said arbitrary sample is set at a glossiness of 0, referring to data (Glo, vs Xso and Yso) obtained from said glossiness sensing and output means when said arbitrary sample is exposed to the light from said standard light source, and also referring to decision data obtained from said decision data storing means, to acquire by performing the arithmetic operation the color and equivalent wavelength ($\lambda eq$) for said sample, and to acquire by performing the arithmetic operation the color difference threshold for said sample at the wavelength which corresponds to said equivalent wavelength.

BRIEF DESCRIPTION OF THE DRAWINGS

FIGS. 5(*a*), 5(*b*) and 5(*c*) show the ratio of the red, green, and blue paints in terms of the chroma when the glossiness is kept at 80%.

DESCRIPTION OF THE PREFERRED EMBODIMENTS

Figure 1:
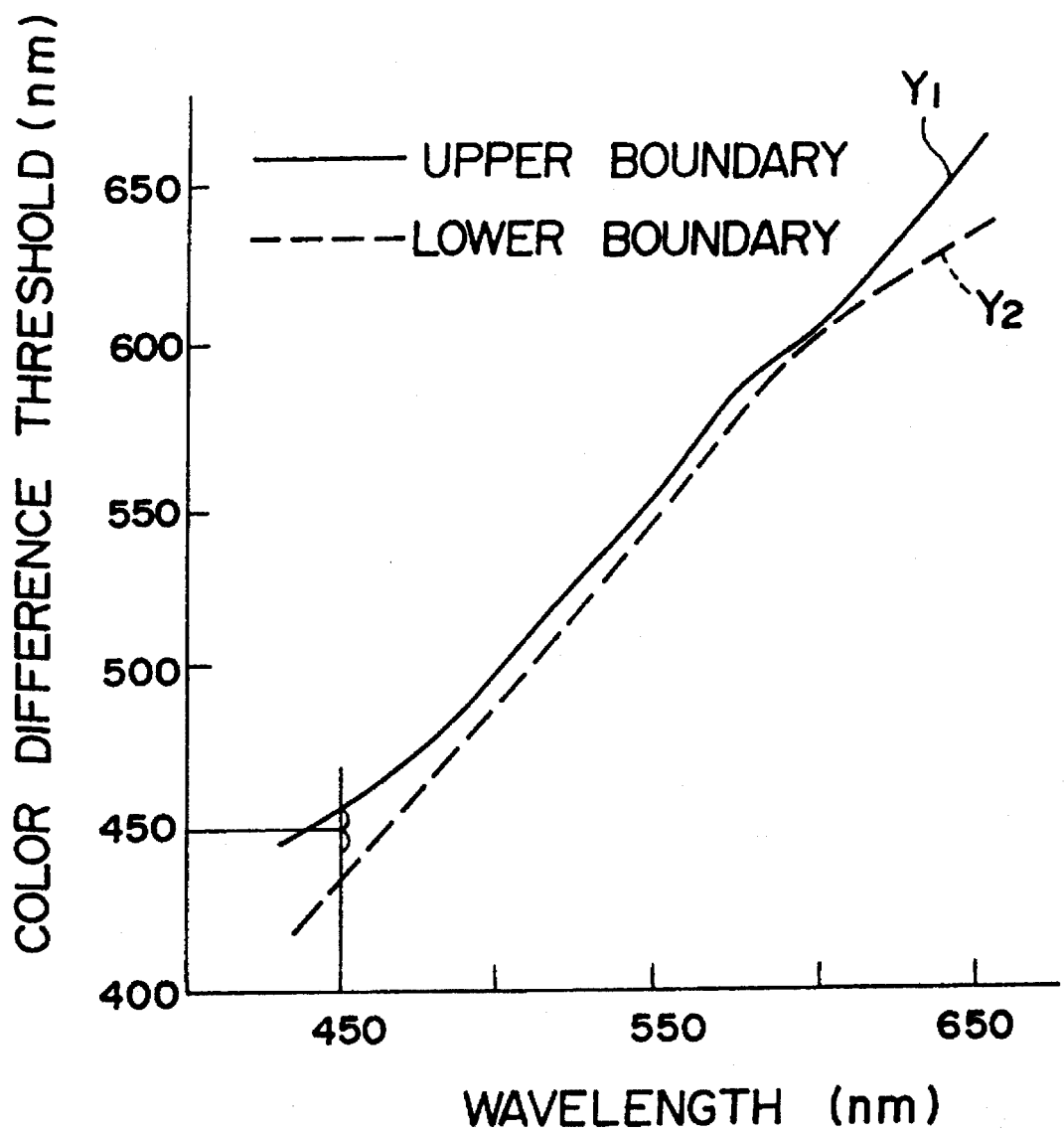
FIG. 1 shows the lower and upper boundaries of color difference thresholds, which are given in terms of wavelength.

The present invention will be described in detail referring to the drawings.

Figure 2:
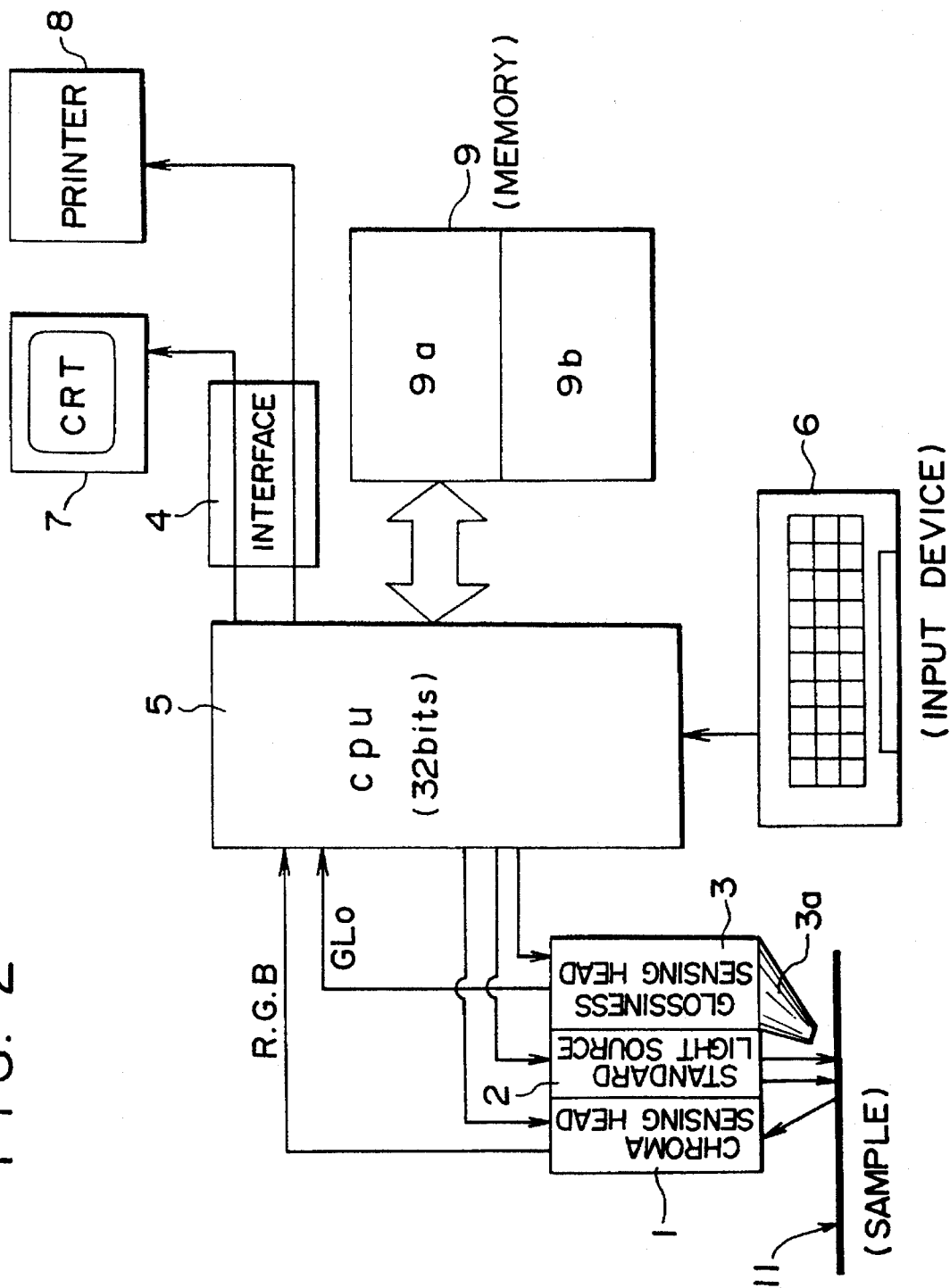
FIG. 2 shows a block diagram of an embodiment of the apparatus for acquiring chroma and glossiness of a sample, which is built in accordance with the present invention.

FIG. 2 shows an embodiment of the apparatus for acquiring data used to evaluate or reproduce the color of a sample on the basis of the chroma and glossiness of the sample in accordance with the present invention.

Sample 11 is exposed to and illuminated by the light from a standard light source 2, and data is acquired from chroma and glossiness sensing heads 1 and 3. Chroma and glossiness sensing heads 1 and 3 constitute the chroma and glossiness sensing means. Memory 9 in decision data storing means stores some kind of data (which will be described hereafter) and the programs used for automatically making a decision of whether the chroma and glossiness of a material are the same as those of a sample. The arithmetic operation means consisting of CPU 5 (of 32 bits) calculate data used to evaluate or reproduce the color of a sample on the basis of the chroma and glossiness of the sample which have been obtained from said chroma and glossiness sensing heads 1 and 3.

Such input device 6 as a keyboard provides instructions to the apparatus. Results and statuses are output from CPU 5 onto CRT 7 and printer 8 through interface 4.

A Xenon lamp which is the same light source as used in the invention disclosed in Japanese patent disclosure number 1992-232821 is used as standard light source 2 to illuminate sample 11.

A CCD imager of the interline type, consisting of 768(H) by 493(V) dots, having a horizontal resolution of 330 lines was used in chroma sensing head 1. The CCD imager outputs 3 prime color components (channels) of sample 11 when said sample 11 is exposed to the light from said light source 2.

Figure 3:
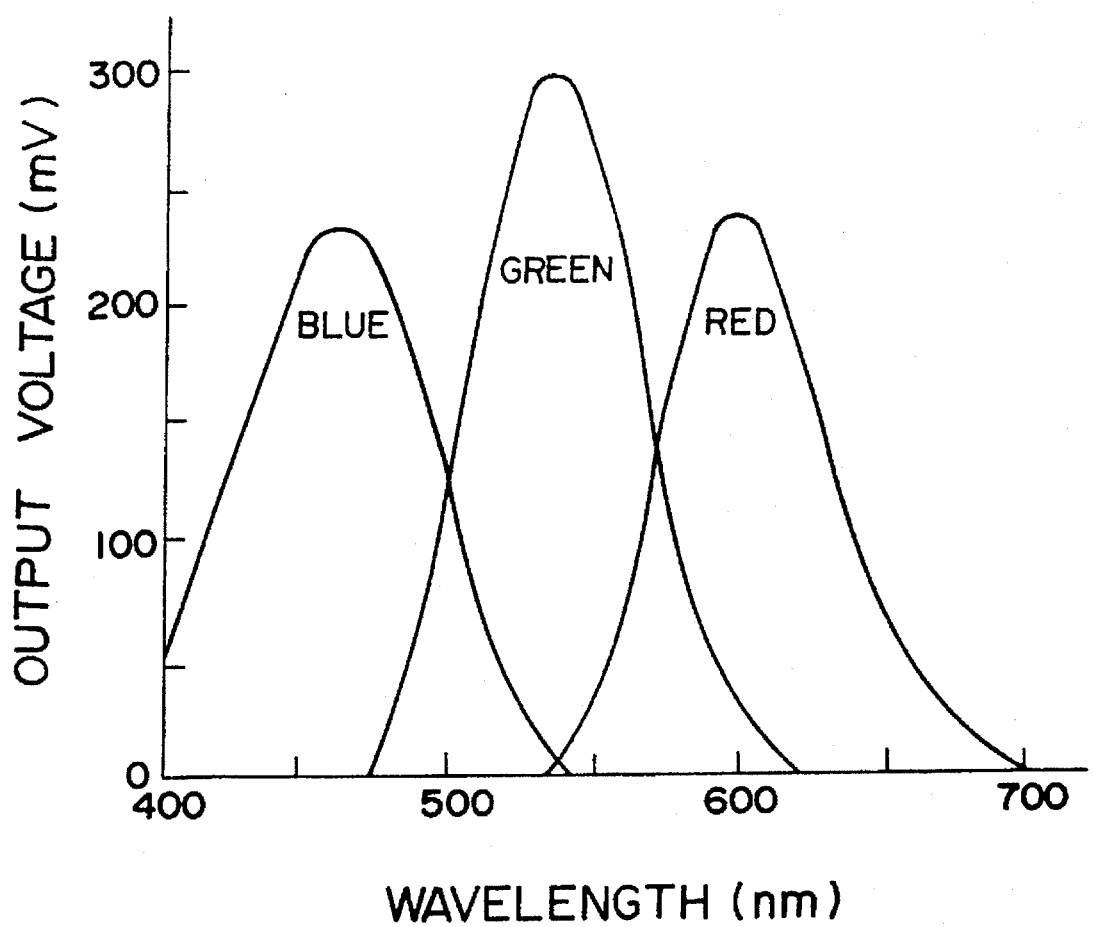
FIG. 3 shows the output voltages of the red, green, and blue color sensors in the chroma sensing head of FIG. 2.

A green (G) filter, a red (R) and a blue (B) filter are alternately arranged to pick up the three prime color (R, G, and B) of an image. FIG. 3 shows the spectral response of chroma sensing head 1.

In FIG. 3, the output voltages of said CCD imager indicate the responses to 3 prime color colors (R, G, and B) when the sample is separately exposed to red, green, and blue colors in sequence. This characteristic has been described in the prescribed applications and will briefly be described hereafter.

The maximum output voltage (i.e., approximately 300 mV) obtained on the green channel of the CCD imager is assigned as 255 in 8 bits. The output voltages on the other channels (i.e., red and blue channels) are digitized referring to the maximum value (255) on the green channel. These digital number in 8 bits are stored in memory 9b. Table 1 lists the contents of memory 9b and the color difference thresholds. A relatively large CCD imager was used in the embodiment because data acquisition was more convenient. A set of compact color sensors for red, green, and blue colors can be used in place of the large CCD imager.

Glossiness sensing means 3 receive the light reflected from said sample 11 when said sample 11 is exposed to and illuminated by said light source 2, and then acquires the glossiness data for said sample 11.

Light guide 3a is used to lead the reflected light from the sample to a photoelectric conversion device (not shown) for measuring the glossiness.

Although the photoelectric conversion device (not shown) for measuring the glossiness is used in the present embodiment, the CCD imager constituting chroma sensing means can be used for this purpose. If the chroma and glossiness signals are alternately picked up from the CCD imager in accordance with the time sharing scheme, data of chroma and glossiness can be acquired from the CCD imager without using a second CCD imager.

The glossiness is normally measured referring to the NBS standard, and however the NBS standard needs not be used for the measurement of the incident and reflection angles for acquiring data from said sample if the apparatus of the present invention is used for this purpose.

Decision data storing means 9 include memory 9b for storing various data which is used for making a decision of whether the chroma and glossiness of a material are the same as those of a sample. Memory 9b stores data on said red, green, and blue channels of said chroma sensing head 1 in terms of the specific wavelengths ($\lambda_s$), and data in memory 9b is as listed in Table 1.

Plots $Y_1$ and $Y_2$ in FIG. 1 indicate the subjective equivalent color boundaries at different wavelengths, and they are as given in expressions (1) and (2) which are described above. The smaller one of a pair of spans ($\Delta\lambda$) in the lower and upper boundaries is given as ($\pm\Delta\lambda$). Since the smaller one of the pair of spans is employed only for simplicity, those in the lower and upper boundaries can separately be used for these expressions ($Y_1$ and $Y_2$).

Said memory 9b stores the normalized outputs (Rso, Gso, Bso) obtained from the outputs (Rs, Gs, Bs) of the red, green, and blue channels of said chroma sensing head 1 in terms of the glossiness and wavelength. The normalization is carried out referring to the maximum output on the green channel in accordance with the prescribed procedure. These outputs are obtained from a plurality of mark plates used as samples in terms of the equivalent wavelength ($\lambda$eq) in addition to the chroma, glossiness, hue, and lightness.

The equivalent wavelength ($\lambda$eq) is defined in the present invention as the wavelength which represents the color of the corresponding sample. When the sample is characterized by a specific color consisting of a plurality of wavelengths, the equivalent wavelengths represent that specific color.

Any sample with a color at wavelengths which are different from those which define the specific color can be recognized as the specific color by human eyes in some cases. These samples can then be handled as those characterized by the same equivalent wavelength ($\lambda$eq). Let this type of equivalent wavelength ($\lambda$eq) correspond to the prescribed wavelength ($\lambda_s$).

The equivalent wavelength ($\lambda$eq) is given by a function of both a plurality of wavelengths ($\lambda i$), which constitute a specific color, and the magnitudes (ci) of the respective wavelengths as $$\lambda eq = f(\Sigma ci \cdot \lambda i)$$

The equivalent wavelength which can be obtained from said red, green, and blue sensors is input to said memory 9a as part of the memory contents.

Memory 9b is installed in a second CPU which is different from that used for arithmetic operation means 5. The second CPU is installed in the second 32 bit personal computer, wherein a pseudo color board (not shown) is provided for use with display CRT 7, and is connected through RS232C cable 4 to display CRT 7 and printer 8 whereto the levels of the chroma and glossiness which have been identified by said 32 bit CPU are output. The levels of the chroma and glossiness are thereafter stored in a floppy disk as measured data.

When the color on the painted surface of a material is output on display CRT 7 after output to printer 8, the actually displayed color depends on the nature of display CRT 7 due to the unique nature of display CRT 7 on the red, green, and blue channels. The colors of the products are thus not uniform. The color on display CRT 7, which corresponds to the wavelengths thereof, is approximated by the pseudo color which has been set by adjustment during visual inspection.

Arithmetic operation means 5 consisting of a 32 bit CPU performs the processing of the color obtained from sample 11 by using chroma sensing head 1, and also the processing of said glossiness obtained from said sample 11 by using glossiness sensing head 3 in order to generate the red, green, and blue components of the color with some glossiness.

After the processing, arithmetic operation means 5 obtain the outputs (Rso, Gso, and Bso) by eliminating the glossiness (Glo.) of said sample 11 from the outputs of the red, green, and blue color sensors in said chroma sensing head 1, referring to said automatic processing program 9a and memory table 9b.

When the operator inputs an instruction from input device 6, the results of the arithmetic operation are displayed on display CRT 7 or printed out on printer 8.

Acquisition of data by means of said devices, and configuration of the database (or the contents of memory 9a) will be described hereafter.

Table 1 lists the color signal (RGB) outputs and color difference thresholds in terms of the wavelength ($\lambda$s). The color signal outputs are the normalized CCD color imager outputs.

The peak output voltage Gs of the green color sensor is assigned to $2^8(=255)$ for normalizing the CCD color imager outputs, and the output voltages of the respective color sensors are in proportion to the peak output voltage Gs of the green color sensor. The color difference threshold at each wavelength ($\lambda$s) is defined by $\pm\Delta\lambda$.

Referring to Table 1, the output voltages ($\lambda$sRso, $\lambda$sGso, and $\lambda$sBso) of the red, green, and blue color sensors are 22, 223, and 0 at a wavelength ($\lambda$s) of 550 nm, respectively, when the 550 nm light power is generated from the standard light source.

Tables 2 through 5 list the normalized red, green, and blue sensor outputs (Rso, Gso, and Bso) obtained from a set of samples produced as mark plates defined by Japan Color Research Institute.

The contents of Tables 1 through 5 are stored in the decision data storing means.

The contents of Tables 1 through 5 will be described hereafter in sequence.

Table 2 lists the outputs of the red, green, and blue color sensors in terms of the glossiness. Assume that the glossiness is specified as 0, 20, 40, 60, and 80%. If the chroma, hue, and lightness are kept unchanged, the color sensor outputs (Rso, Gso, and Bso) increase as the lightness increases. The color sensor outputs are proportional to the lightness.

Assume that the glossiness is specified as 0, 20, 40, 60, and 80%. If the chroma, hue, and lightness are kept unchanged, for instance, as for sample 5R4/12 on the red channel, the equivalent wavelength ($\lambda$eq) representing the color of each sample does not change. For samples 5G4/6 (on the green channel) and 5B4/6 (on the blue channel), the same relation holds.

Table 3 lists the outputs of the red, green, and blue color sensors in terms of the chroma. Assume that the chroma is specified as 2, 4, 6, 8, 10, and 12. If the glossiness (80%), hue, and lightness are kept unchanged, the color sensor outputs (Rso, Gso, and Bso) increase as the chroma increases.

Assume that the chroma is specified as 2, 4, 6, 8, 10, and 12. If the glossiness (80%), hue, and lightness are kept unchanged, the equivalent wavelength ($\lambda$eq) representing the color of each sample does not change.

Table 4 lists the outputs of the red, green, and blue color sensors in terms of the lightness and wavelength ($\lambda$eq).

Assume that the chroma, glossiness, and hue are specified as 12, 80%, and 5R, respectively. If the lightness is specified as 4, 5, and 6, the equivalent wavelengths ($\lambda$eq) for these lightness values are respectively 586, 588, and 590. The red, green, and blue color sensor outputs (Rso, Gso, and Bso) increase as the lightness increases. The color sensor outputs are proportional to the lightness.

For samples on the green and blue channels, the same relation holds.

Table 5 lists the outputs of the red, green, and blue color sensors in terms of the lightness unless the chroma is specified. When the lightness is 2 unless the chroma is specified (or monochrome), the color sensor outputs (Rso, Gso, and Bso) on the red, green, and blue channels are 42, 42, and 42, respectively. When the lightness is 9 in the monochrome case, the color sensor outputs (Rso, Gso, and Bso) on the red, green, and blue channels are 248, 248, and 248, respectively. As the lightness increases, the color sensor outputs on the red, green, and blue channels increase. The ratio of the red, green, and blue color sensor outputs is unity (1:1:1) on the monochrome sample. For the monochrome sample, the red, green, and blue sensor outputs do not change even if the glossiness changes when the lightness is kept unchanged. When the lightness is specified as 2 if the glossiness is in the range of 0 to 80%, the red, green, and blue color sensor outputs are 42, 42, and 42, respectively. When the lightness is specified as 9 if the glossiness is in the range of 0 to 80%, the red, green, and blue color sensor outputs are 248, 248, and 248, respectively.

Figure 4:
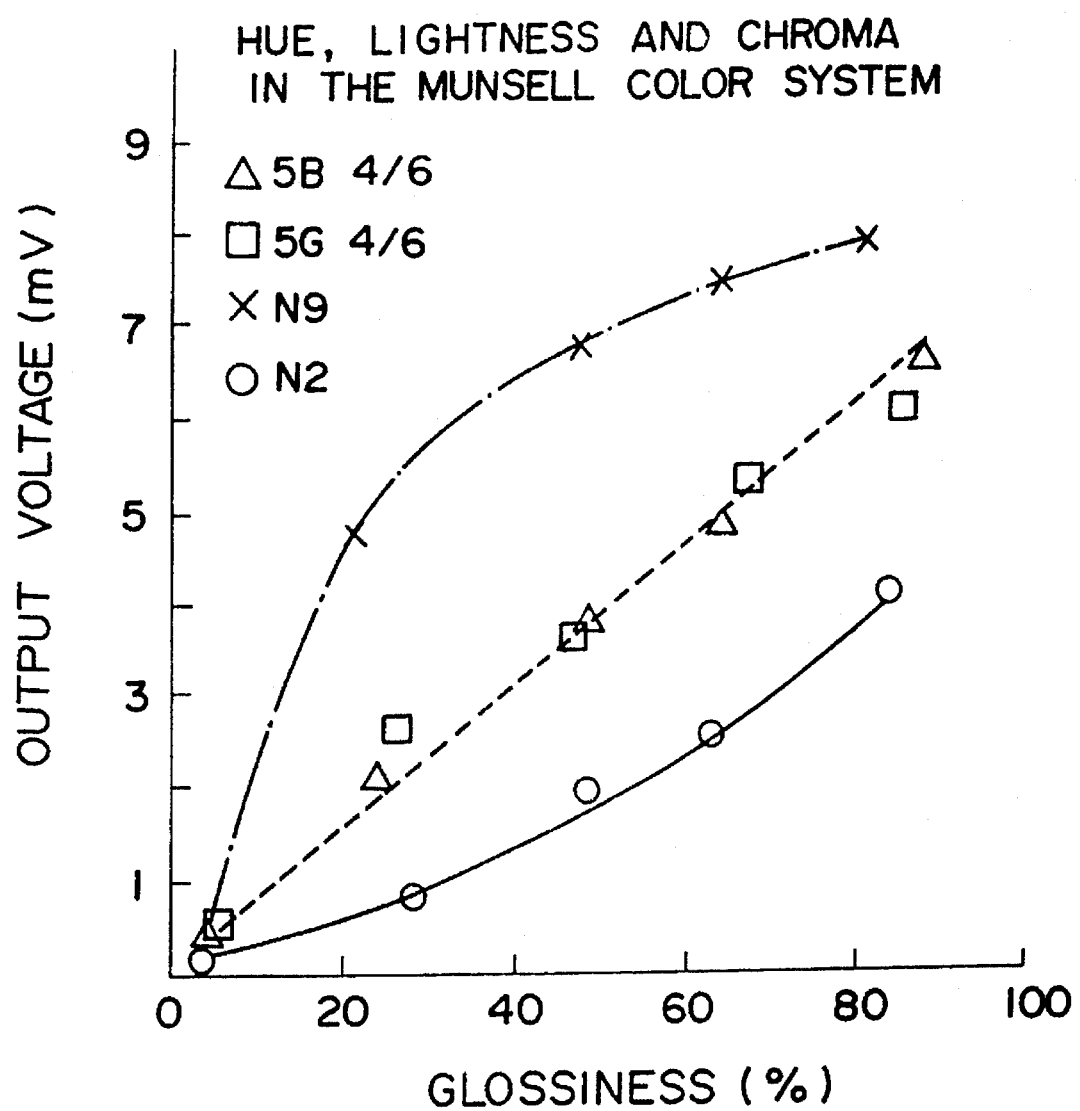
FIG. 4 shows the output voltages of the red, green, and blue color sensors in terms of the glossiness for a variety of chroma, hue, and lightness.

FIG. 4 shows the output voltage changes in terms of the glossiness for a variety of samples. The sensor output voltages for both the colored (5B4/6 and 5G4/6) and monochrome (N2 and N9) samples increase as the glossiness increases. For the colored samples, the output voltages are proportional to the glossiness.

The output voltages for a monochrome sample of N9 are greater than those for the colored samples at a specified glossiness in the range of 5 to 90%, however the output voltages for a monochrome sample of N2 are less than those for the colored samples at a specified glossiness in the range of 5 to 90%. A plot for a sample with gray color will run in the area surrounded by the plots for N2 and N9.

These measured values are used as basic data for calculating the glossiness on the 32 bit microprocessor.

FIGS. 5(*a*), 5(*b*) and 5(*c*) show the red, green, and blue color sensor outputs for samples with different chroma levels when the glossiness is kept unchanged at 80%. When the chroma goes to 0, the sensor outputs approach the specific values defined for the monochrome signal.

If a material is exposed to the light, the reflected light power is determined depending on the glossiness of the reflecting surface. That is, the magnitude of the light power reflected from the surface due to normal reflection increases as the glossiness increases, and that due to random reflection increases as the glossiness decreases.

The glossiness is decided by sensing the magnitude of the reflected light power through the optical fiber opto-electronic sensor.

The algorithm to acquire evaluation data from the chroma and glossiness of the sample will be described hereafter. This algorithm is stored in memory 9*a* as a program for automatically calculating evaluation data.

The basic algorithm for the evaluation is to numerically obtain the output voltages of the red, green, and blue color sensors at a glossiness of 0.

(1) An arbitrary sample is to be exposed to the light from the standard light source. Data (Glo. vs Rso, Gso, and Bso) obtained from the output voltages of chroma and glossiness sensing heads 1 and 3 in terms of the glossiness is to be compared with that obtained from said decision data storing means.

(2) Data (Rso0, Gso0, and Bso0) is to be calculated for a glossiness of 0% which is specified for said arbitrary sample.

Assume that data (Glo. vs Rso, Gso, Bso)=(80%, 170, 58, 50) is obtained from the output voltages of said chroma and glossiness sensing heads 1 and 3. This corresponds to 5R4/12 on Table 2. Then, data (Glo.0 vs Rso0, Gso0, Bso0)=(0%, 160, 51, 40) can be obtained from the calculation.

Data obtained from the output voltages of said chroma and glossiness sensing means 1 and 3 seldom fit that stored in memory 9*b* for Table 2. Evaluation data can thus be obtained from the extrapolation or interpolation of data stored in memory 9*b* for Table 2.

A decision for the hue to which the sample belongs is made based on data calculated by using the basic algorithm for the evaluation. If the sample belongs to red in hue, the following calculation can be done.

Rso0=170×160/170=160
Gso0=58×160/170=55
Bso0=50×160/170=47

Where, 160/170 in the above example is the glossiness reduction ratio.

How to combine the red, green, and blue paints in order to reproduce the desired color at the specified glossiness will be described hereafter.

Assume evaluation data at a glossiness of 0% (Glo.0 vs Rso0, Gso0, Bso0) is given as (0%, 160, 51, 40). The ratio of combination of the red, green, and blue paints is then to be 160, 51, and 40 if said evaluation data is used for reproducing the desired color at a specified glossiness of 0%.

Let the quantities of the red, green, and blue paints required for painting a unit area of surface be Rg, Gg, and Bg, respectively. These quantities will be given as Rg=$f_{rg}$(160), Gg=$f_{gg}$(51), and Bg=$f_{bg}$(40). Where, $f_{jkg}$ are the specific functions of the respective chroma levels with positive gradients. Assume that each function is a linear function of a chroma level with a unity coefficient. The quantities of the red, green, and blue paints are directly given by evaluation data as Rg=160, Gg=51, and Bg=40, respectively.

These paints are to be combined together in a solvent in order to obtain the paint for reproducing the desired color. After the painting is completed, the glossiness is to be set at 80% by coating the painted surface with a clearing agent.

The color of part of the painted surface is to be used as evaluation data for the painting. Data (Glo vs Rso, Gso, Bso) entered into the system as evaluation data is to be compared with specified values (80%, 170, 58, 50) so that the difference between them can easily be read.

Another equivalent wavelength (λ'eg) resulting from the reproduced color of the painted surface is to be used for evaluating the quality of said reproduced color, and it should be within (λeq±Δλ). The contents of Table 1 are to be used to compare the equivalent wavelength (Δeq) with the other one (Δ'eq).

If the monochrome surface is desired for the painting, the ratio of the red, green, and blue color sensors should be 1:1:1.

APPLICATIONS

As described heretofore, the apparatus built in accordance with the present invention acquires data which is used to reproduce the chroma of a sample in accordance with the chroma and glossiness of the sample. The reproduced color of the sample can automatically be evaluated by utilizing standard data for the color sensation of human eyes of a specific race.

Both the color adjustment and evaluation for the paintings, which were conventionally carried out by skilled craftsman, can automatically be done by the apparatus of the present invention.

The difference in both chroma and glossiness between the painted surface of the body of an automobile after a repaired portion is painted, and the original surface whereon no overcoats are painted after the repairing can easily be recognized. The quality of the products whereon color materials are painted can easily be inspected without intervention of any skilled personnel or without the use of special processes, if the apparatus of the present invention is used for the inspection. In addition, the quality of the products whereon color materials are painted can be improved by the apparatus of the present invention.

TABLE 1

Color signal outputs and color difference thresholds in terms of the wavelength.

| WAVELENGTH | RGB OUTPUTS | | | COLOR DIFFERENCE THRESHOLD |
|---|---|---|---|---|
| λ s (nm) | λ sRso | λ sGso | λ sBso | λ s (nm) ± Δλ |
| 410 | 0 | 0 | 67 | 410 ± 14 |
| 420 | 0 | 0 | 95 | 420 ± 14 |
| 430 | 0 | 0 | 125 | 430 ± 12 |
| 440 | 0 | 0 | 154 | 440 ± 11 |
| 450 | 0 | 0 | 181 | 450 ± 10 |
| 460 | 0 | 0 | 196 | 460 ± 9 |
| 470 | 0 | 0 | 195 | 470 ± 9 |
| 480 | 0 | 13 | 179 | 480 ± 9 |
| 490 | 0 | 50 | 155 | 490 ± 8 |
| 500 | 0 | 93 | 116 | 500 ± 8 |
| 510 | 0 | 158 | 67 | 510 ± 7 |
| 520 | 0 | 213 | 37 | 520 ± 6 |
| 530 | 0 | 252 | 14 | 530 ± 6 |
| 540 | 8 | 252 | 3 | 540 ± 5 |
| 550 | 22 | 223 | 0 | 550 ± 4 |
| 560 | 51 | 186 | 0 | 560 ± 3 |
| 570 | 93 | 130 | 0 | 570 ± 3 |
| 580 | 143 | 82 | 0 | 580 ± 2 |
| 590 | 188 | 51 | 0 | 590 ± 2 |
| 600 | 200 | 30 | 0 | 600 ± 2 |
| 610 | 185 | 14 | 0 | 610 ± 2 |
| 620 | 153 | 3 | 0 | 620 ± 2 |
| 630 | 121 | 0 | 0 | 630 ± 3 |
| 640 | 85 | 0 | 0 | 640 ± 4 |
| 650 | 61 | 0 | 0 | 650 ± 5 |
| 660 | 185 | 14 | 0 | 660 ± 6 |
| 670 | 153 | 3 | 0 | 670 ± 7 |

TABLE 2

Outputs of the red, green, and blue color sensors in terms of the glossiness.

| Hue | Lightness/ Chroma | Glossiness (Glo.) | Wavelength (λ eq) | Red Rso | Green Gso | Blue Gso |
|---|---|---|---|---|---|---|
| 5R | 4/12 | 80 (%) | 584 (nm) | 170 | 58 | 50 |
| 5R | 4/12 | 60 | 584 | 166 | 54 | 44 |
| 5R | 4/12 | 40 | 584 | 165 | 53 | 42 |
| 5R | 4/12 | 20 | 584 | 162 | 52 | 41 |
| 5R | 4/12 | 0 | 584 | 160 | 51 | 40 |
| 5G | 4/6 | 80 (%) | 522 (nm) | 85 | 224 | 177 |
| 5G | 4/6 | 60 | 522 | 80 | 216 | 170 |
| 5G | 4/6 | 40 | 522 | 74 | 207 | 162 |
| 5G | 4/6 | 20 | 522 | 73 | 205 | 160 |
| 5G | 4/6 | 0 | 522 | 71 | 196 | 158 |
| 5B | 4/6 | 80 (%) | 498 (nm) | 62 | 117 | 175 |
| 5B | 4/6 | 60 | 498 | 53 | 109 | 170 |
| 5B | 4/6 | 40 | 498 | 52 | 107 | 168 |
| 5B | 4/6 | 20 | 498 | 51 | 105 | 166 |
| 5B | 4/6 | 0 | 498 | 50 | 104 | 163 |

TABLE 3

Outputs of the red, green, and blue color sensors in terms of the chroma (with a glossiness of 80%).

| Hue | Lightness/ Chroma | Wavelength (λ eq) | Red Rso | Green Gso | Blue Bso |
|---|---|---|---|---|---|
| 5R | 4/12 | 584 (nm) | 170 | 58 | 50 |
| 5R | 4/10 | 584 | 156 | 87 | 78 |
| 5R | 4/8 | 584 | 154 | 89 | 87 |
| 5R | 4/6 | 584 | 150 | 99 | 97 |
| 5R | 4/4 | 584 | 148 | 115 | 115 |
| 5G | 4/10 | 522 (nm) | 58 | 232 | 165 |
| 5G | 4/8 | 522 | 68 | 228 | 175 |
| 5G | 4/6 | 522 | 85 | 224 | 177 |
| 5G | 4/4 | 522 | 121 | 214 | 195 |
| 5G | 4/2 | 522 | 123 | 207 | 197 |
| 5B | 4/10 | 498 (nm) | 46 | 128 | 195 |
| 5B | 4/8 | 498 | 54 | 119 | 187 |

TABLE 3-continued

Outputs of the red, green, and blue color sensors in terms of the chroma (with a glossiness of 80%).

| Hue | Lightness/Chroma | Wavelength ($\lambda$ eq) | Red Rso | Green Gso | Blue Bso |
|-----|------------------|---------------------------|---------|-----------|----------|
| 5B  | 4/6              | 498                       | 62      | 117       | 175      |
| 5B  | 4/4              | 498                       | 64      | 115       | 150      |
| 5B  | 4/2              | 498                       | 70      | 107       | 119      |

TABLE 4

Outputs of the red, green, and blue color sensors in terms of the lightness and wavelength (with a glossiness of 80%).

| Hue | Lightness/Chroma | Wavelength ($\lambda$ eq) | Red Rso | Green Gso | Blue Bso |
|-----|------------------|---------------------------|---------|-----------|----------|
| 5R  | 6/12             | 590 (nm)                  | 238     | 132       | 111      |
| 5R  | 5/12             | 588                       | 193     | 78        | 72       |
| 5R  | 4/12             | 586                       | 170     | 58        | 50       |
| 5G  | 5/6              | 526 (nm)                  | 142     | 242       | 226      |
| 5G  | 4/6              | 522                       | 85      | 224       | 177      |
| 5G  | 3/6              | 518                       | 78      | 183       | 158      |
| 5G  | 2/6              | 502                       | 56      | 109       | 99       |
| 5B  | 7/6              | 512 (nm)                  | 89      | 171       | 216      |
| 5B  | 6/6              | 510                       | 78      | 158       | 205      |
| 5B  | 4/6              | 498                       | 62      | 117       | 175      |
| 5B  | 3/6              | 497                       | 58      | 105       | 158      |
| 5B  | 2/6              | 494                       | 54      | 87        | 116      |

TABLE 5

Outputs of the red, green, and blue color sensors in terms of the lightness.

| lightness | Glossiness | Red Rso | Green Gso | Blue Bso |
|-----------|------------|---------|-----------|----------|
| 2         | 80 (%)     | 42      | 42        | 42       |
| 2         | 60         | 42      | 42        | 42       |
| 2         | 40         | 42      | 42        | 42       |
| 2         | 20         | 42      | 42        | 42       |
| 2         | 0          | 42      | 42        | 42       |
| 9         | 80 (%)     | 248     | 248       | 248      |
| 9         | 60         | 248     | 248       | 248      |
| 9         | 40         | 248     | 248       | 248      |
| 9         | 20         | 248     | 248       | 248      |
| 9         | 0          | 248     | 248       | 248      |

What is claimed is:

1. Apparatus for acquiring data to evaluate a reproduced sample in accordance with the chroma and glossiness thereof comprising:

a standard light source;

chroma sensing means, said chroma sensing means acquiring chroma data (Rso, Gso, and Bso) from three prime color sensors (Rs, Gs, and Bs) when said sample is exposed to light from said standard light source;

glossiness sensing means, said glossiness sensing means acquiring glossiness data (Glo) from said sample upon receiving a component of light reflected by said sample when said sample is exposed to light from said light source;

decision data storing means for storing chroma data acquired by said chroma sensing means and glossiness data acquired by said glossiness sensing means for each of a plurality of mark plates, said mark plates being prepared for a variety of colors and degrees of glossiness while exposed to light from said standard light source; and storing equivalent wavelengths ($\lambda$eq) of the mark plates and upper and lower thresholds thereof, said thresholds being determined by experiments conducted by a specific group of humans having the same eye color; and arithmetic operation means to output an equivalent wavelength ($\lambda$eq) of said sample by comparing said chroma and glossiness data (Rso, Gso, Bso and Glo) of the sample to corresponding data stored in said decision data storing means.

2. Apparatus as claimed in claim 1 wherein said standard light source is a Xenon lamp.

3. Apparatus as claimed in claim 1 wherein said chroma sensing means is a CCD color imager.

4. Apparatus as claimed in claim 2 wherein said chroma sensing means is also used as a glossiness sensing means.

* * * * *